United States Patent [19]

Tam

[11] Patent Number: 5,463,721
[45] Date of Patent: * Oct. 31, 1995

[54] METHOD FOR CONSTRUCTING A THREE DIMENSIONAL SCANNING TRAJECTORY CAPABLE OF ACQUIRING A COMPLETE SET OF RADON DATA FOR EXACT IMAGE RECONSTRUCTION OF AN OBJECT IRRADIATED BY A CONE BEAM SOURCE

[75] Inventor: Kwok C. Tam, Schenectady, N.Y.

[73] Assignee: General Electric Company, Schenectady, N.Y.

[ * ] Notice: The portion of the term of this patent subsequent to Dec. 17, 2008 has been disclaimed.

[21] Appl. No.: 737,117

[22] Filed: Jul. 29, 1991

[51] Int. Cl.$^6$ .................................................. G06T 17/00
[52] U.S. Cl. .................... 395/127; 395/119; 364/413.13; 364/413.15; 364/413.16
[58] Field of Search ...................................... 395/119, 120, 395/121, 124, 125, 126, 127; 364/413.13–413.16; 324/309

[56] References Cited

U.S. PATENT DOCUMENTS

| | | | |
|---|---|---|---|
| 4,985,677 | 1/1991 | Pauly | 324/309 |
| 5,068,882 | 11/1991 | Eberhard | 378/4 |
| 5,073,910 | 12/1991 | Eberhard et al. | 378/4 |
| 5,124,914 | 6/1992 | Grangeat | 364/413.16 |

OTHER PUBLICATIONS

Cone–Beam Tomography: Recent Advances and a Tutorial Review, Bruce D. Smith, Optical Engineering, May 1990, vol. 29, No. 5, pp. 524–534.
Image Reconstruction From Cone–Beam Projections: Necessary and Sufficient Conditions and Reconstruction Methods, Bruce D. Smith, IEEE Transactions on Medical Imaging, Mar. 1985, vol. MI–4, No. 1, pp. 14–25.
An Inversion Formula for Cone–Beam Reconstruction, Heang K. Tuy, Siam J. Appl. Math., Jun. 1983, vol. 43, No. 3, pp. 546–552.
Convolutional Reconstruction From Cone–Beam Projection Data, Gerald N. Minerbo, IEEE Transactions on Nuclear Science, vol. NS–26, No. 2, Apr. 1979, pp. 2682–2684.
Practical Cone–Beam Algorithm, L. A. Feldkamp, L. C. Davis, and J. W. Kress, J. Opt. Soc. Am. A, vol. 1, No. 6, Jun. 1984, pp. 612–619.
P. Grangeat, "Analysis of a 3D Imaging System by Reconstruction from X–Radiographies in Conical Geometry," Ph.D. Thesis, National College of Telecommunications (l'Ecole Nationale Superieure des Telecommunications), France (1987) [translation enclosed].

Primary Examiner—Almis R. Jankus
Attorney, Agent, or Firm—Paul R. Webb, II

[57] ABSTRACT

Construction and assessment methods provide a three dimensional scanning trajectory to ensure the acquisition of a complete set of Radon data for exact image reconstruction of an object irradiated by a cone beam source is described. The three dimensional scanning trajectory must be nowhere disconnected permitting the source to traverse the scanning trajectory in a continuous manner from start point to end point. The trajectory defines edges wherein a convex surface is formed by connecting these edges, this surface is known as a convex hull. If the convex hull defined by a trajectory encloses the object to be scanned, a complete set of Radon data for exact image reconstruction of the object can be acquired. This provision amounts to satisfying the three dimensional completeness criterion. Furthermore, if any planar projection of the trajectory encloses the corresponding planar projection of the object, the three dimensional completeness criterion is satisfied by using projected planar visualization aids.

8 Claims, 10 Drawing Sheets

METHOD FOR CONSTRUCTING A THREE DIMENSIONAL SCANNING TRAJECTORY CAPABLE OF ACQUIRING A COMPLETE SET OF RADON DATA FOR EXACT IMAGE RECONSTRUCTION OF AN OBJECT IRRADIATED BY A CONE BEAM SOURCE

CROSS-REFERENCE TO RELATED APPLICATIONS

The invention disclosed and claimed herein is related to the subject matter of the following commonly-assigned patent applications, the entire disclosures of which are hereby expressly incorporated herein by reference:

Co-pending application, now U.S. Pat. No. 5,383,119 filed Jun. 28, 1991 by Kwok C. Tam entitled "METHOD AND APPARATUS FOR ACQUIRING COMPLETE RADON DATA FOR EXACTLY RECONSTRUCTING A THREE DIMENSIONAL COMPUTERIZED TOMOGRAPHY IMAGE OF A PORTION OF AN OBJECT IRRADIATED BY A CONE BEAM SOURCE";

Co-pending application Ser. No. 07/631,815, filed Dec. 21, 1990, by Kwok C. Tam, entitled "METHOD AND APPARATUS FOR CONVERTING CONE BEAM X-RAY PROJECTION DATA TO PLANAR INTEGRALS AND RECONSTRUCTING A THREE-DIMENSIONAL COMPUTERIZED TOMOGRAPHY (CT) IMAGE OF AN OBJECT";

Co-pending application Ser. No. 07/631,818, filed Dec. 21, 1990, by Kwok C. Tam, entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRALS";

Co-pending application Ser. No. 07/572,651, filed Aug. 27, 1990, by Jeffrey W. Eberhard et al, entitled "SQUARE WAVE CONE BEAM SCANNING TRAJECTORY FOR DATA COMPLETENESS IN THREE DIMENSIONAL COMPUTERIZED TOMOGRAPHY";

Co-pending application Ser. No. 07/572,590, filed Aug. 27, 1990, by Jeffrey W. Eberhard et al, entitled "DUAL PARALLEL CONE BEAM CIRCULAR SCANNING TRAJECTORIES FOR REDUCED DATA INCOMPLETENESS IN THREE-DIMENSIONAL COMPUTERIZED TOMOGRAPHY"; and Co-pending application Ser. No. 07/631,514, filed Dec. 21, 1990 by Kwok C. Tam, entitled "METHOD AND APPARATUS FOR RECONSTRUCTING A THREE-DIMENSIONAL COMPUTERIZED TOMOGRAPHY (CT) IMAGE OF AN OBJECT FROM INCOMPLETE CONE BEAM PROJECTION DATA".

BACKGROUND OF THE INVENTION

The present invention relates generally to three dimensional (3D) computerized tomography (CT) and more specifically to methods for constructing and assessing a three dimensional scanning trajectory to ensure the acquisition of a complete set of Radon data for exact image reconstruction of an object irradiated by a cone beam source.

Conventional CT employs a technique for obtaining cross sectional slices of an object from planar parallel or fan beam irradiation of an object. The technique is primarily utilized in medical and industrial diagnostics. Traditional image reconstruction techniques have been predominantly two dimensional. In three dimensions, an undistorted image of an object can be mathematically reconstructed in an exact manner by back projecting a parallel beam which has been attenuated after passing through the object using an inverse transform based on the Fourier Slice Theorem. The use of a parallel beam source and a flat two dimensional detector geometrically simplifies reconstruction but complicates practical considerations having to do with speed and ease of data collection.

Back projections can be mathematically accomplished for a 3D cone beam source by inverse Radon transforming suitable planar integrals. The planar integrals are computed from detector integrals which utilize measured cone beam projection data i.e. the detected attenuated intensity representative of the density distributions of the irradiated object. The use of a 3D cone beam source expedites data acquisition, but complicates geometrical considerations when used with a flat detector.

In two dimensions, the analog of cone beam source geometry is illustrated by fan beam geometry. For the case of fan beam geometry, the detector integral are equivalent to the Radon transform of the object. Unlike the two dimensional case, a direct Radon inversion of three dimensional cone beam data from a cone beam source is not possible. Before the inverse Radon transform can be undertaken in three dimensions, the cone beam detector integrals must be reconfigured into planar integrals suitable for inverse Radon transformation. Due to such limitations, three dimensional CT imaging has usually involved stacking slices representative of the density distribution through the object obtained from various parallel or fan beam attenuation projections. Each projection is associated with a particular view angle or configuration of source and detector relative to the object. A data set is generally acquired by either rotating a source and detector, fixed relative to each other, around an object taking projections as the object is scanned; or alternatively, rotating the object between the fixed source and detector.

The three dimensional Radon inversion problem was addressed in two commonly assigned patent applications: U.S. patent application Ser. No. 07/631,815 filed Dec. 18, 1990 by Kwok C. Tam entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT discloses method and apparatus for converting cone beam data to values representing planar integrals on any arbitrary set of planes in Radon space for 3D image reconstruction through inverse Radon transformation. A related U.S. patent application Ser. No. 07/631,818 filed on Dec. 21, 1990 by Kwok C. Tam entitled PARALLEL PROCESSING METHOD AND APPARATUS FOR RECONSTRUCTING THREE-DIMENSIONAL COMPUTERIZED TOMOGRAPHY (CT) IMAGE OF AN OBJECT FROM CONE BEAM PROJECTION DATA OR FROM PLANAR INTEGRALS discloses a two step approach for performing an inverse Radon transform from planar integrals obtained on a plurality of coaxial planes. The first step involves calculating from the planar integrals a two dimensional projection image of the object on each of the coaxial planes; while the second step involves defining normal slices through these coaxial planes from which a two dimensional reconstruction of each slice is obtained. In this slice by slice way, the reconstruction algorithms operate on the plurality of planar integrals to produce a three dimensional image of the object.

It is further essential to note that the acquired data set is complete only if it provides sufficient Radon data at every necessary point in Radon space, i.e. Radon space must be sufficiently filled with data over the region of support in Radon space which corresponds to that region of support in object space occupied by the object. Radon data is generally acquired by exposing the entire object within the field of view of a source and scanning about the object using a source fixed with respect to a corresponding detector to obtain measurements. Sufficient filling of Radon space by a candidate scanning configuration is necessary for exact image reconstruction. Furthermore, if the detector integral space is filled over the region of support for the object, the Radon data set is complete. Bruce D. Smith in an article entitled "Image Reconstruction from Cone-Beam Projections: Necessary and Sufficient Conditions and Reconstruction Methods," IEEE Trans. Med. Imag., MI-4 (1985) 14, has shown that a cone beam data set is complete if each plane passing through the object cuts the scanning trajectory in at least one point. This criterion assumes that the detector is fixed relative to the source and that the entire object can be scanned within the field of view of the source. Depending on the scanning configuration employed to obtain the cone beam projection data, the data set in Radon space may or may not be complete. Utilizing an incomplete data set for image reconstruction by Radon inversion introduces artifacts which compromise image quality and may render the image inadequate for medical or industrial diagnostic use.

A scanning configuration comprising two circular trajectories whose axes of rotation are normal with respect to one another is suggested by Gerald N. Minerbo, "Convolutional Reconstruction from Cone-Beam Projection Data", IEEE Trans. Nucl. Sci., Vol. NS-26, No. 2, pp. 2682–2684 (April 1979); and Heang K. Tuy, "An Inversion Formula for Cone-Beam Reconstruction", SIAM J. Math., Vol. 43, No. 3, pp. 546–552 (June 1983). Smith points out in his 1985 article that this trajectory satisfies the completeness criterion. Although complete, this scanning configuration is not practical as it is mechanically difficult to implement. A much easier to implement complete scanning trajectory has been disclosed in commonly assigned U.S. patent application Ser. No. 07/572,651, filed Aug. 27, 1990, by Eberhard et al entitled "SQUARE WAVE CONE BEAM SCANNING TRAJECTORY FOR DATA COMPLETENESS IN THREE-DIMENSIONAL COMPUTERIZED TOMOGRAPHY". Although incomplete, the scanning geometry most commonly adopted is the circular scanning trajectory which engulfs the entire object in the field of view of the source. A circular scanning configuration which minimizes data incompleteness by utilizing more than one circular scan path is disclosed in commonly-assigned U.S. patent application Ser. No. 07/572,590, filed Aug. 27, 1990, by Eberhard entitled "DUAL PARALLEL CONE BEAM CIRCULAR SCANNING TRAJECTORIES FOR REDUCED DATA INCOMPLETENESS IN THREE DIMENSIONAL COMPUTERIZED TOMOGRAPHY".

One can attempt to compensate for an inherently incomplete scanning trajectory using apriori corrections. Commonly assigned U.S. patent application Ser. No. 07/572,590 discloses an apriori approach to reducing the effects of incompleteness on three dimensional cone beam reconstruction by correcting two dimensional projection images obtained on each of a plurality of coaxial planes in Radon space using optically obtained object boundary information. From this, a three dimensional image is reconstructed on slices normal to the common axis in a slice by slice manner using two dimensional reconstruction on each slice.

Generally, no easy to implement, method for assessing whether a source scanning trajectory satisfies the completeness criterion has been disclosed which can accommodate exact image reconstruction in three dimensions when cone beam geometry is employed. Three dimensional exact image reconstruction is by its very nature computationally intensive; therefore, ensuring that data is collected in a manner that sufficiently fills the necessary volume of Radon space without unduly escalating the complexity of practical data acquisition provides a significant improvement over the existing art. As a practical consideration, efficient scanning also minimizes dose exposure to the object being scanned.

A typical scanning and data acquisition configuration employing cone beam geometry is depicted in FIG. 1. An object 20 is positioned within the field of view between a cone beam point source 22 and a typical two dimensional detector array 24, which provides cone beam projection data. An axis of rotation 26 passes through the field of view and the object 20. For purpose of analysis, a midplane 28 is defined normal to the axis of rotation 26 which contains the cone beam point source 22. By convention, the axis of rotation 26 is generally taken to be the z axis, having its origin at its intersection with the midplane. The (x,y,z) coordinate system is fixed relative to the source 22 and detector 24. In scanning the object 20 at a plurality of angular positions, the source 22 moves relative to the object and the field of view typically rotates along a circular scanning trajectory 30 lying in the midplane 28, while the detector 24 remains fixed with respect to the source 22 (or alternatively the object 20 can be rotated while the source 22 and detector 24 remain stationary). Data is acquired at a plurality of source positions during the scan. Data collected at the detector 24 represent line integrals through the object 20. The approach to reconstruction then embodies calculating planar integrals on a set of planes from various line integrals through the object, then performing an inverse Radon transform on these planar integrals to reconstruct a three dimensional image of the object.

It has already been established that data collected using a commonly adopted single circular scan is incomplete and artifacts may accordingly be introduced into the reconstructed image. Dual parallel circular scanning trajectories have been shown to reduce data set incompleteness. A circular square wave scanning trajectory, as well as, dual mutually perpendicular circular scanning trajectories provide a complete Radon data set for exact image reconstruction having been shown to satisfy the completeness criterion as articulated by Smith. More recently, Bruce D. Smith in an article entitled "Cone-beam Tomography: Recent Advances and a Tutorial Review", Optical Engineering, Vol. 29, No. 5, pp. 524–534, May 1990, mentions several complete scanning trajectories. However, Smith's statement of the completeness criterion which asserts that any plane through the object must intersect at least one point on the scanning trajectory is not easy to visualize nor practical to implement for candidate scanning trajectories.

SUMMARY OF THE INVENTION

In accordance with the invention, it is recognized that a scanning trajectory must satisfy the completeness criterion for data completeness in three dimensions; wherein the statement of the completeness criterion asserts that each plane passing through the object, cuts the scanning trajectory in at least one point.

Accordingly, it is an object of the invention to provide a practical, visual, method for constructing a three dimensional scanning trajectory so as to ensure that Radon data set acquired therefrom satisfies the completeness criterion; thereby guaranteeing exact reconstruction of a unique three dimensional image of an object irradiated by a cone beam scanning source.

It is accordingly a further object of the invention to provide practical, visual, methods for assessing a three dimensional scanning trajectory in order to determine whether Radon data acquired therefrom satisfies the completeness criterion thereby guaranteeing exact reconstruction of a unique three dimensional image of an object irradiated by a cone beam scanning source.

In accordance with the invention, each of these methods provides a three dimensional scanning trajectory which is nowhere disconnected permitting a source to traverse the scanning trajectory in a continuous manner from start point to end point in such a way that the trajectory satisfies the completeness criterion in three dimensions. Satisfaction of the completeness criterion in three dimensions can be accomodated by utilizing the three dimensional scanning trajectory to visually define the edges of an external surface, said surface forming a three dimensional convex hull enclosing the object. Such enclosure is sufficient to satisfying the completeness criterion in three dimensions. Furthermore, any planar section through the object necessarily intersects the convex hull in satisfaction of the completeness criterion. In addition, any planar projection of said three dimensional convex hull which encloses the corresponding planar projection of said object, equivalently satisfies the completeness criterion.

It is another object of the invention to enlarge the practical utility of Smith's statement of the completeness criterion by satisfying the above mentioned easy to visualize criterion for characterizing in two dimensions the completeness of a candidate three dimensional scanning trajectory.

It is a further object of the invention to make completeness assessment practical and simple to implement by determining whether the completeness criterion is satisfied in three dimensions through the utilization of easy to visualize planar projections.

It is a still further object of the invention to provide such a method which may be readily implemented in commonly adopted scanning trajectories without unduly escalating complexity, cost or dose.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION OF THE INVENTION

Figure 1:
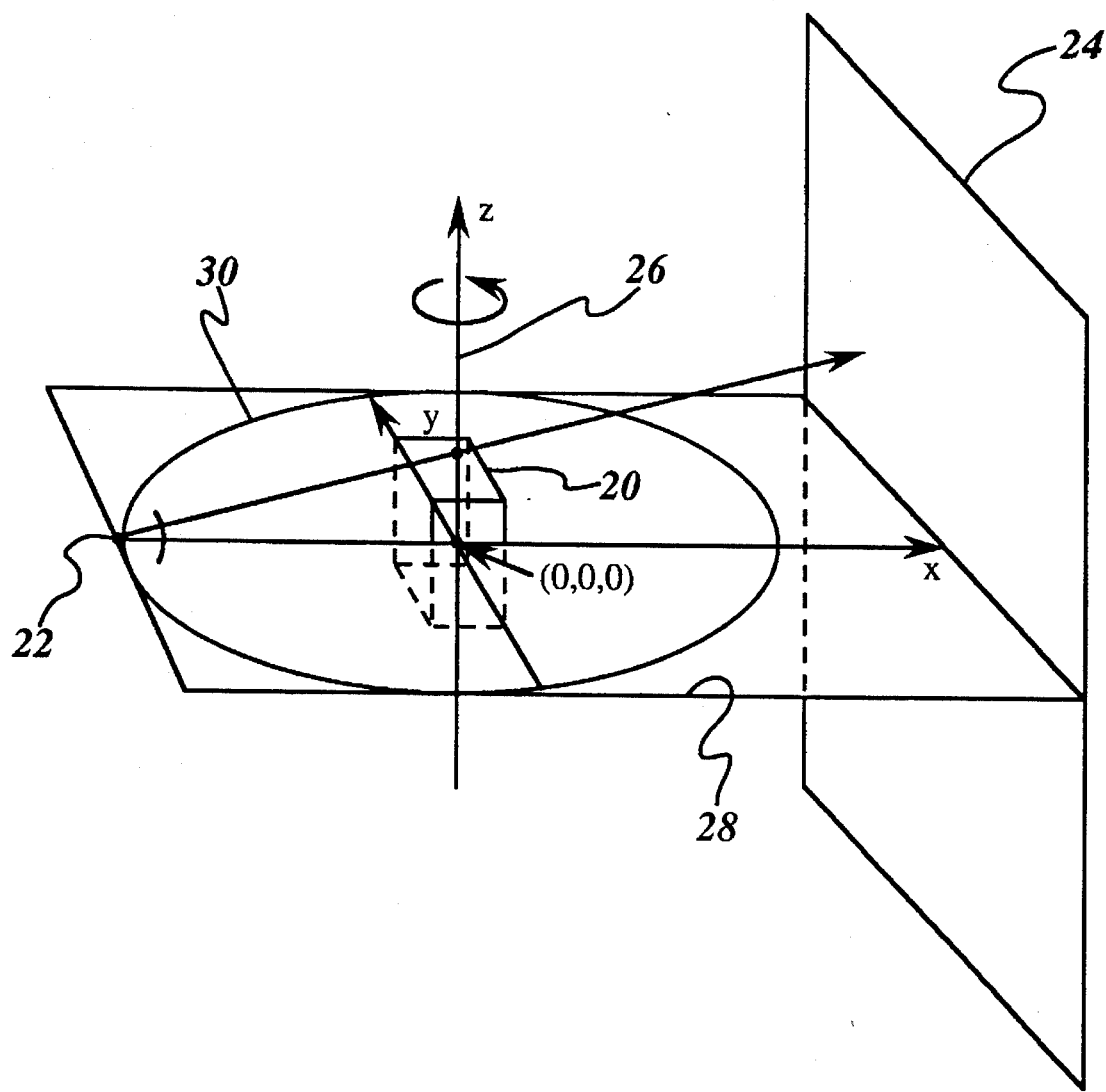
FIG. 1 referred to hereinabove, represents conventional cone beam scanning geometry for three dimensional CT imaging.

Since the present invention is directed to providing methods for ensuring that a scanning trajectory is capable of acquiring a complete set of Radon data, what is meant by data completeness will be discussed followed by a description of the methods for constructing and assessing a three dimensional scanning trajectory in accordance with the invention.

It is critical to note that a Radon data set is complete if it provides sufficient data at every point in Radon transform space; or stated another way: if Radon space is sufficiently filled with data over the region of support corresponding to the field of view in real space within which the object of interest fits, the Radon data set is complete. Thus, filling the detector integral space over the region of support for the object results in a complete Radon data set. However; the extent to which filling of Radon space occurs depends on the specific source scanning configuration selected for acquiring data. The scanning configuration presumes the source is fixed relative to a corresponding detector and scanned about an object in a relative manner i.e. either the source/detector arrangement is scanned about a fixed object, or alternatively, the object is scanned about a fixed source/detector arrangement. Furthermore, the scanning configuration generally presumes the object being scanned is enclosed within the field of view of the source; although this need not necessarily be the case (See co-pending U.S. Pat. No. 5,383,119. For the sake of illustration the object will herein be assumed to be completely enclosed within the field of view of the cone beam source. Smith (1985) has stated the completeness criterion by asserting that a cone beam data set is complete if there is a point from the cone beam source scanning trajectory on each plane passing through the object of interest. This statement of the completeness criterion is not easy to visualize in three dimension and therefore cannot be readily applied to the assessment of scanning trajectories. The invention herein articulates a three dimensional topological statement of the completeness criterion which can easily be visualized by projection in two dimensions providing an easy method for assessing completeness in candidate scanning trajectories. Illustrations of applying the criteria to some examples of complete scanning trajectories will be presented.

In accordance with the invention, in three dimensions a sufficient condition for the availability of complete information in cone beam scanning is that a three dimensional scanning trajectory must nowhere be disconnected i.e. the scanning trajectory must accommodate continuous scanning from start point to endpoint, and that the three dimensional scanning trajectory define the edges of a convex connected surface or 'convex hull' enclosing the object being scanned.

It is imperative to recognize that the externally defined convex surface formed by connecting all points of each segment of a candidate three dimensional scanning trajectory to all points of each respective remaining segment, is termed a 'convex hull'.

Figure 2:
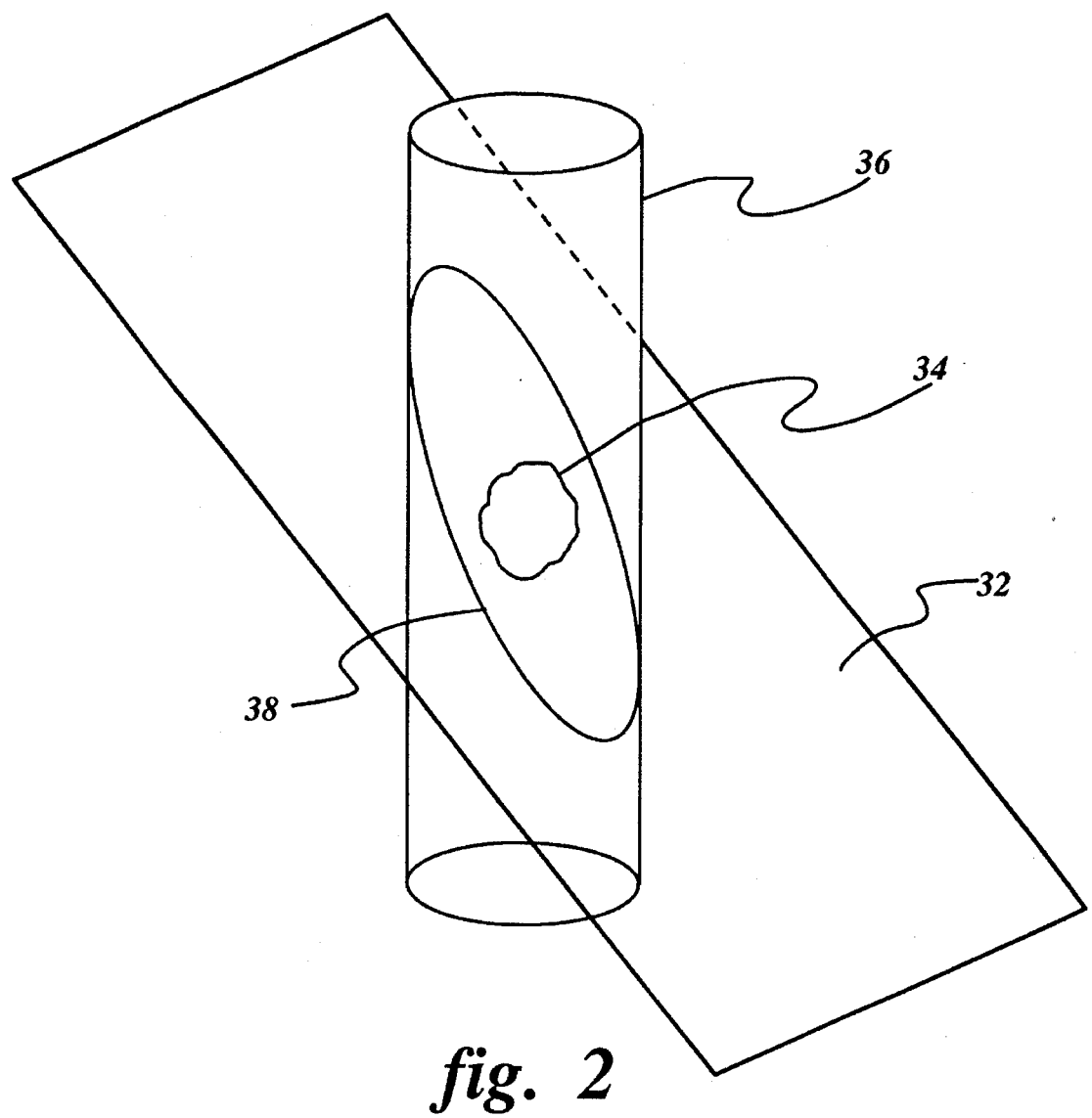
FIG. 2 illustrates a planar intersection through the convex hull of a typical three dimensional scanning trajectory which is nowhere disconnected, showing the planar section enclosing the object in accordance with the invention.

For the sake of illustration consider the scanning trajectory to be comprised of two parallel circular scan paths connected by a linear scan segment. As shown in FIG. 2, any plane 32 intersecting the object 34 must intersect the boundary of convex hull 36. Convex hull 36 for this illustrative scan trajectory is clearly a cylinder. The curve of intersection between plane 32 and convex hull 36 is identified at numeral 38. If none of the points on the scanning trajectory can be found on the curve of intersection 38, then the plane 32 must partition the scanning trajectory. This is impossible since the scanning trajectory is assumed to be nowhere disconnected being capable of continuous scanning from start point to end point. Thus, any plane intersecting the convex hull must cut the scanning trajectory in at least one point and the completeness criterion is therefore satisfied. In accordance with the method herein disclosed a three dimensional scanning trajectory which is nowhere disconnected is provided wherein a source is capable of scanning the object in a continuous manner from start point to end point. The edges of said trajectory define a convex hull such that any planar section through the object being scanned necessarily intersects the convex hull; thus enclosing said object.

Figure 3:
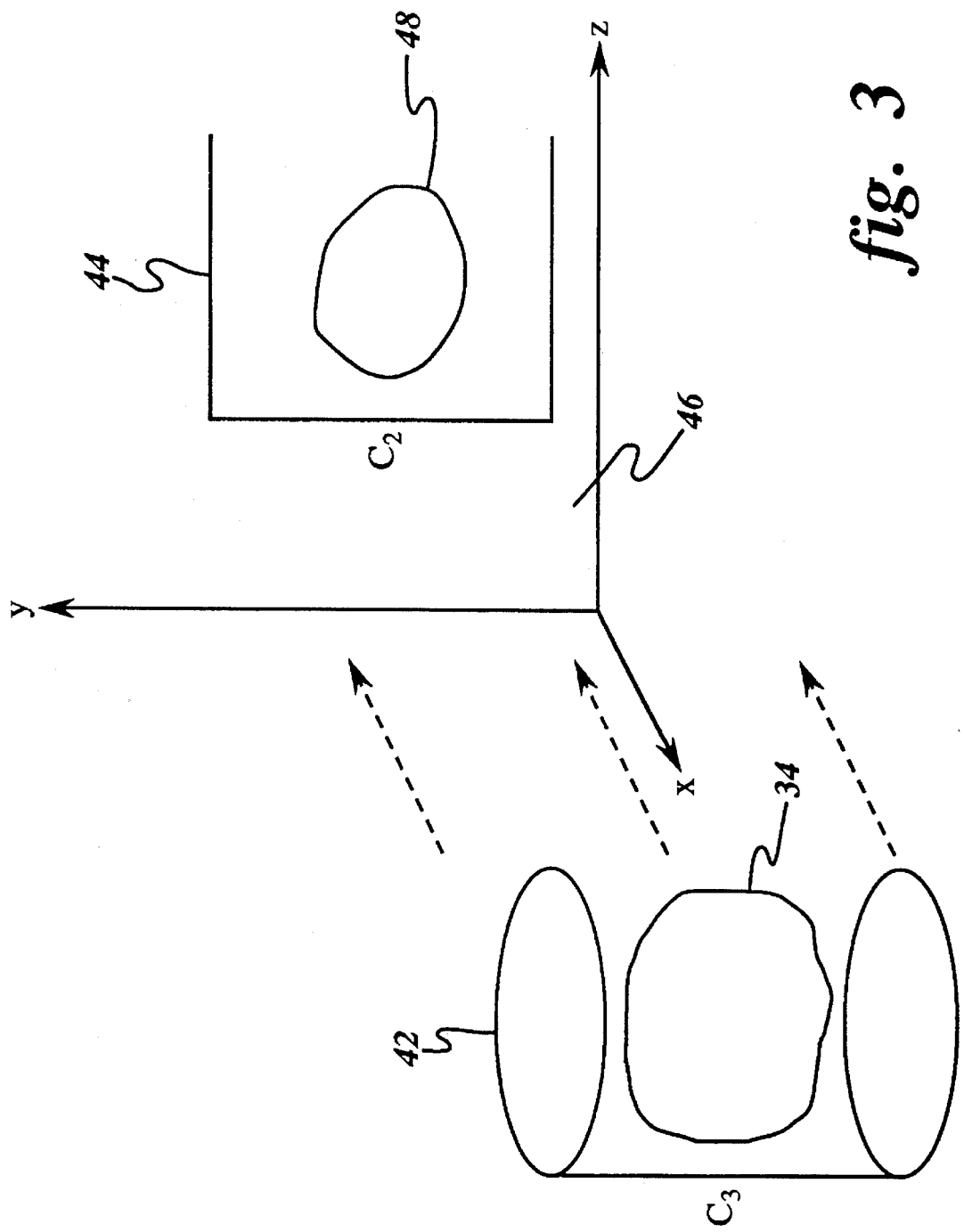
FIG. 3 illustrates the convex hull of a connected three dimensional scanning trajectory enclosing an object and a corresponding two dimensional projection thereof onto any vertical plane showing the corresponding two dimensional projection of the object to be completely enclosed thereby in accordance with the invention.

In two dimensions satisfaction of the completeness criterion can be more easily visualized. In FIG. 3, a continuous and nowhere disconnected three dimensional scanning trajectory, $C_3$, taken again to be comprised of two parallel circular scan paths connected by a linear scan segment, for the purpose of illustration, is identified by numeral 42. A two dimensional projection C2 of this candidate three dimensional scanning trajectory is identified by numeral 44 being projected onto any vertical plane 46 (e.g. a plane coaxial with the common axis of the two circular scan paths). The two dimensional scanning trajectory 44 thus projected is continuous from projected start point to projected end point and nowhere disconnected. In accordance with the invention, assessing whether the planar projection 44 of the three dimensional scanning trajectory 42 encloses a planar projection of the object 48 provides an easily visualized two dimensional method for determining whether the completness criterion has been satisfied for a particular scanning trajectory.

Figure 4:
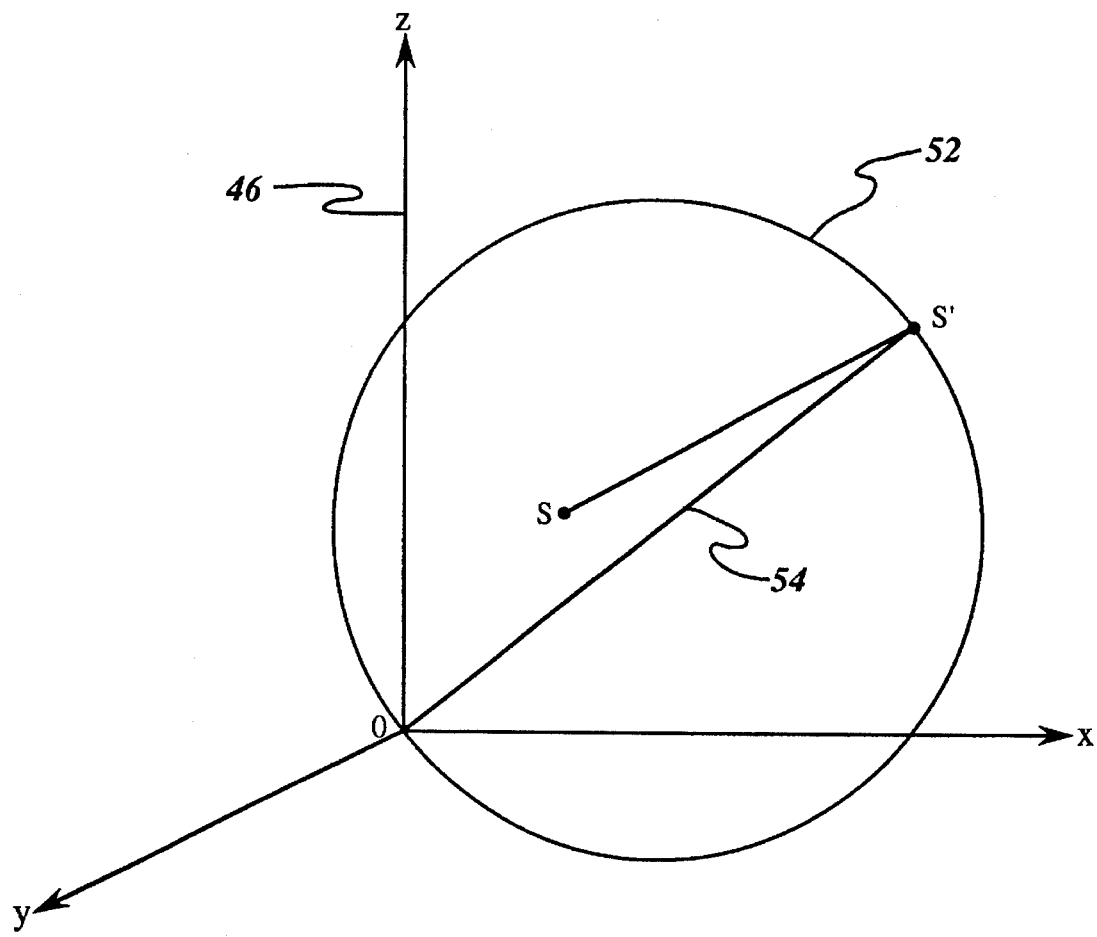
FIG. 4 illustrates Radon data generated on any vertical plane for one position of the cone beam source.

Consider FIG. 4 which depicts a source residing at some point S on a three dimensional scanning trajectory. Radon data generated therefrom resides on a spherical Radon shell associated with that source position (See U.S. patent application Ser. No. 07/631,815). The diameter of this spherical Radon shell is given by the source to object centered origin distance. FIG. 4 illustrates the intersection of such a Radon shell with the same vertical plane 46. Circle 52 identifies this intersection. The origin is indicated by "O" and the source position is indicated by "S". The projection of the source position onto the vertical plane 46 is shown at S' so that the diameter 54 of the Radon shell intersection circle is OS'. The Radon data generated on that particular plane 46 when the source is at position S reside on circle 52 with diameter OS' 54. Coincidentally, a two dimensional fan beam source positioned at S' would generate two dimensional Radon data on the same circle 52 with diameter 54 given by OS'. Consequently in a three dimensional cone beam scan along three dimensional scanning trajectory 42, Radon data are generated on the vertical plane of interest 46 in the same way as Radon data would be generated using a two dimensional fan beam scan along the planar two dimensional scanning trajectory 44. Since the image reconstructed on vertical plane 46 corresponds to the two dimensional projection image 48 of three dimensional object 34, the completeness problem and the data sampling uniformity problem of the cone beam scan can be synthesized and analyzed in the same manner as a two dimensional fan beam scan of the planar projection image 48 along the projected two dimensional scanning trajectory 44.

The condition for complete information in two dimensional CT scanning follows from the central slice theorem, which states that the one dimensional Fourier transform of a projection of a two dimensional object is a line of Fourier components of the object. Consequently one requires the projections of the two dimensional object at all angles in order to reconstruct an image of the object uniquely. Therefore, complete information in two dimensional CT scanning requires the availability of projections of the object at all angles which is equivalent to the condition that every line through any point in the two dimensional object should intersect the closure of the scanning trajectory. This completeness condition is fulfilled if the convex hull of the two dimensionally projected scanning trajectory 44 encloses the two dimensional projection of the object 48. For the case of cone beam scanning, this means that in accordance with the invention a planar projection of the convex hull of three dimensional scanning trajectory 44 must encompass the two dimensional projection image 48 of the three dimensional object.

The analysis just presented can be applied to a variety of three dimensional scanning trajectories. Clearly the number of three dimensional scanning trajectories which an be analyzed within the scope of the present invention is beyond comprehensive treatment. Those three dimensional scanning trajectories discussed herein are only representative of a class of three dimensional scanning trajectories that can be constructed and/or analyzed in accordance with applicant's invention.

Figure 5:
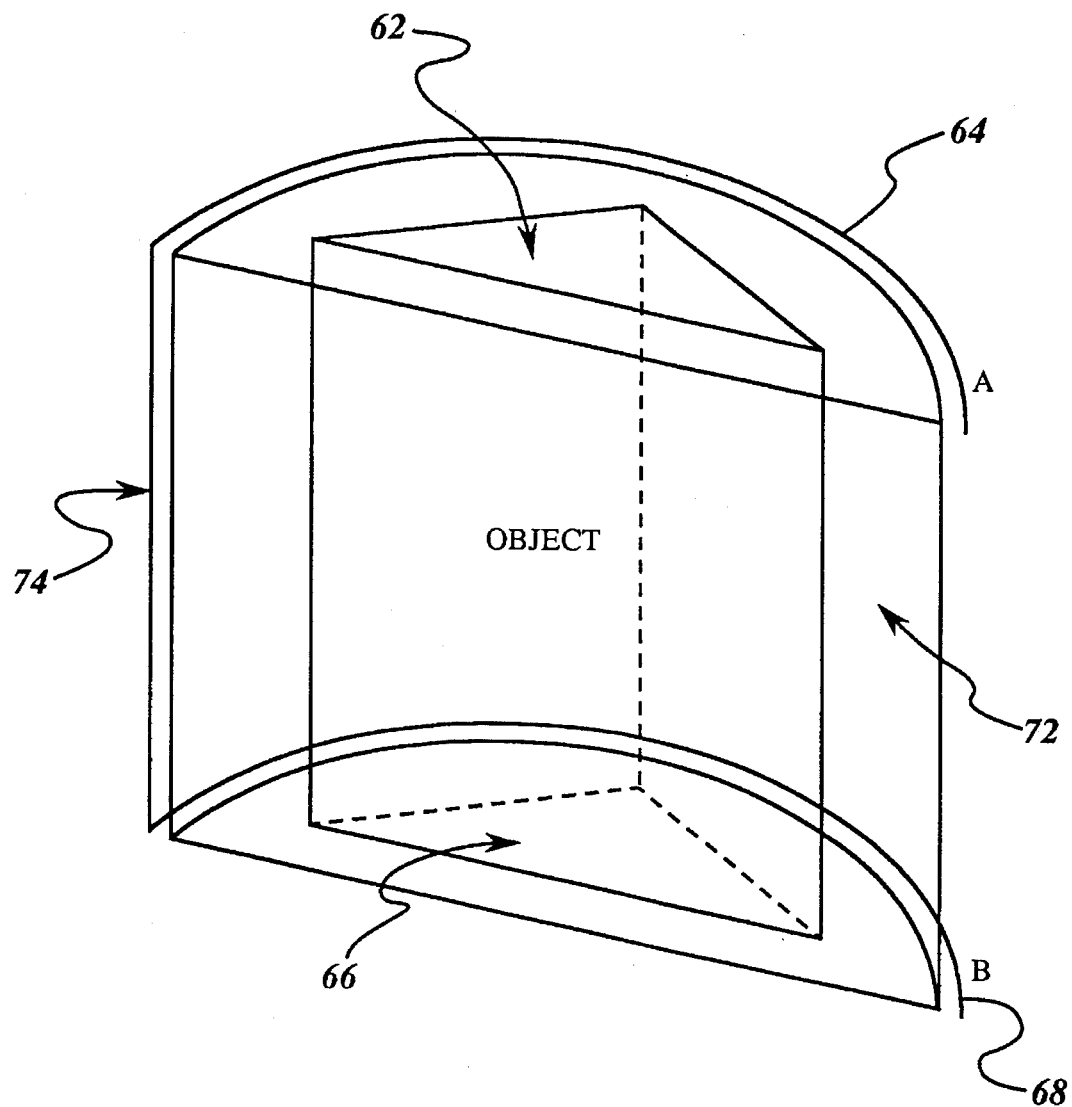
FIG. 5 exemplifies a complete, three dimensional scanning trajectory comprising two circular arcs connected by a line segment wherein the convex hull of this scanning trajectory completely encloses the object.

FIG. 5 presents a scanning trajectory comprised to two arcs connected by a line segment. For the sake of illustration, when the arcs are circular, the convex hull of the scanning trajectory is a truncated cone. For the particular case in which the circular arcs are complete circles of the same radius whose planes are parallel this convex hull is a right circular cylinder as was shown in FIG. 3. The representative scanning trajectory of FIG. 5 will be analyzed according to applicant's completeness assessment showing that if the object is completely contained within the truncated cone constituting the convex hull, then the scanning trajectory is complete.

In two dimensions, the projection of the trajectory on a vertical plane is a convex quadrilateral. If the quadrilateral on every vertical plane contains the projection of the object on that plane, the trajectory is complete. To so ensure, the scanning trajectory can be constructed as follows:

Enclose the upper surface 62 of the object, z=b, inside the smallest segment A 64 that contains the upper surface, and enclose the lower surface 66 of the object, z=±b, inside a segment B 68 that contains the lower surface. By construction, this optimizes flux exposure and minimizes scanning time thus restraining computational requirements.

Figure 6:
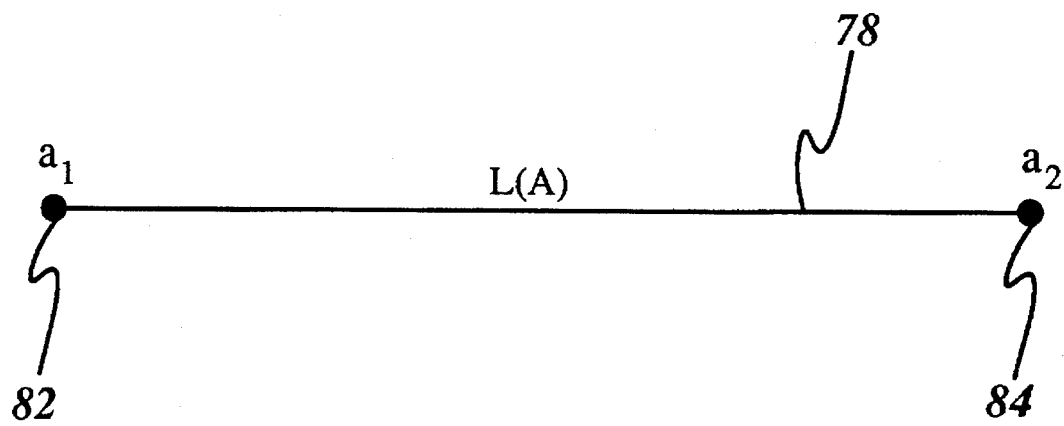
FIG. 6 illustrates a two dimensional projection onto a vertical plane of the circular arcs labelled A and B in the scanning trajectory of FIG. 5.
Figure 6:
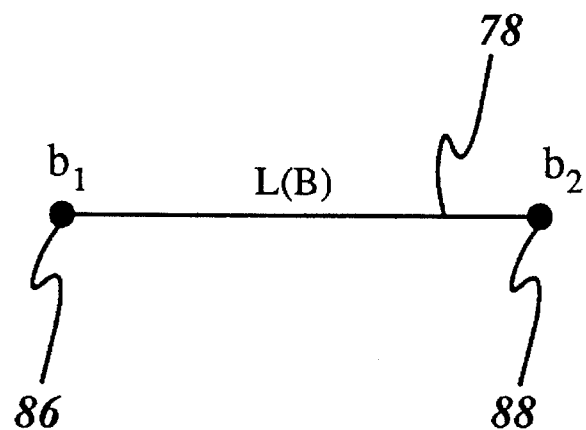
Figure 7:
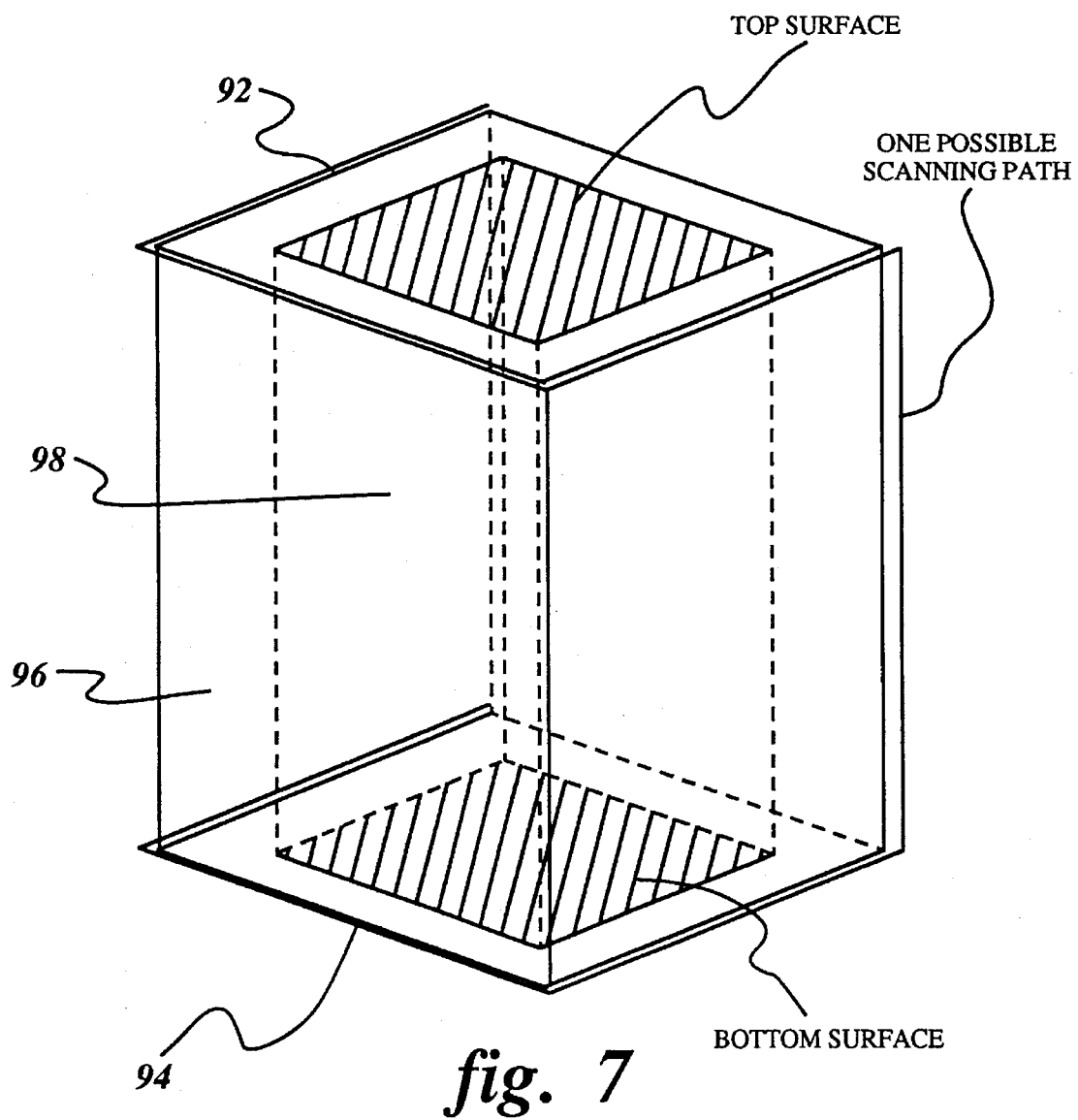
FIG. 7 exemplifies a complete, three dimensional scanning trajectory comprising two open polygons connected by a line segment wherein the convex hull of this scanning trajectory completely encloses the object.

On any projection onto a vertical plane, segments 64 and 66 appear as two straight lines L(A) 76 and L(B) 78, respectively, as shown in FIG. 6. Line segment L(A) has endpoints $a_1$ and $a_2$, as indicated at 82 and 84 respectively. Line segment L(B) has endpoints b1 and b2 as indicated at 86 and 88 respectively. Consider S ($a_1$) and S($a_2$) are two sets of points of segment A that project onto endpoints $a_1$ and $a_2$ respectively. Similarly S($b_1$) and S($b_2$) are two sets of points of segment B that project onto endpoints $b_1$ and $b_2$ respectively. By connecting each point in set S($a_1$) to each point in set S($b_1$) and likewise each point in set S($a_2$) to each point in set S($b_2$), for every vertical projection, a closed region 72 is defined. It is required that the closed region 72 so constructed enclose the object. By construction, at each vertical projection, the projection of the object is enclosed by the convex hull of the projection of the three dimensional scanning trajectory; therefore, the two dimensional version of the completeness criterion is also satisfied. Thus, by combining arc A 64 and arc B 68 with any connecting path 74, usually chosen for convenience to be a linear segment, a complete cone beam scanning trajectory is obtained. There is no requirement that the arcs defining the convex hull be circular. Clearly open polygons like those illustrated in FIG. 7 at 92 and 94 also define an object enclosing convex hull 96. It is the shape of the object itself taken together with practical considerations of mechanical translational and rotational scanning that dictate the geometry of the three dimensional scanning trajectory.

Furthermore, there is no requirement that there be upper and lower encasement surfaces of the convex hull be defined by arcs. The object can be encased just as well by a convex hull defined only by linear segments that are nowhere disconnected. Line scans are easy to implement because they involve only translational motion. Furthermore, with line scans, the projection of uniformly sampled data onto a vertical plane preserves uniformity directly without introducing additional geometrical complexity resulting from commonly adopted circular scans. This property makes data manipulation much easier and more straight forward.

Figure 8:
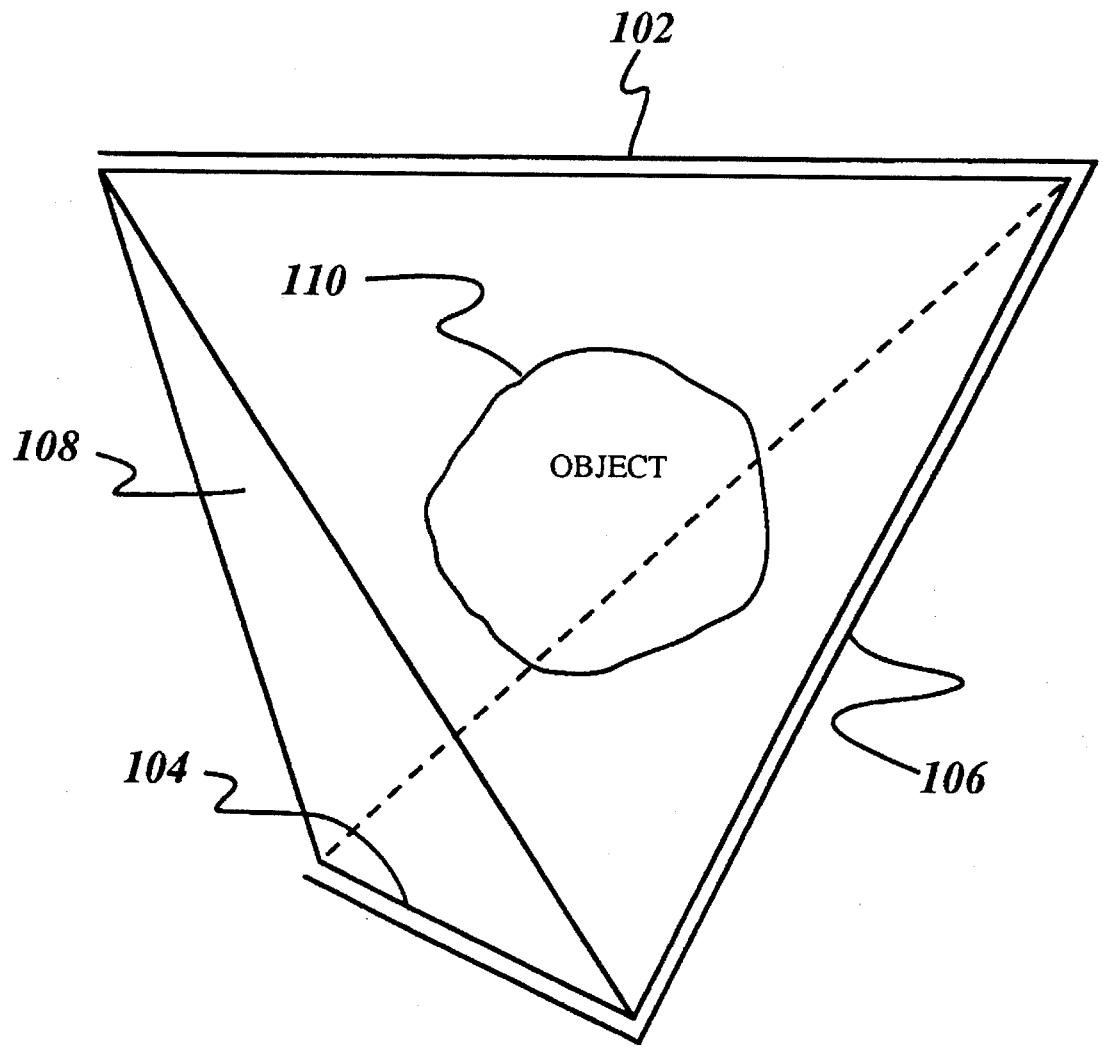
FIG. 8 exemplifies a complete, three dimensional, open scanning trajectory comprising three straight line segments which are nowhere disconnected arranged to accommodate continuous scanning along three non-intersecting edges of a tetrahedron enclosing the object.
Figure 9:
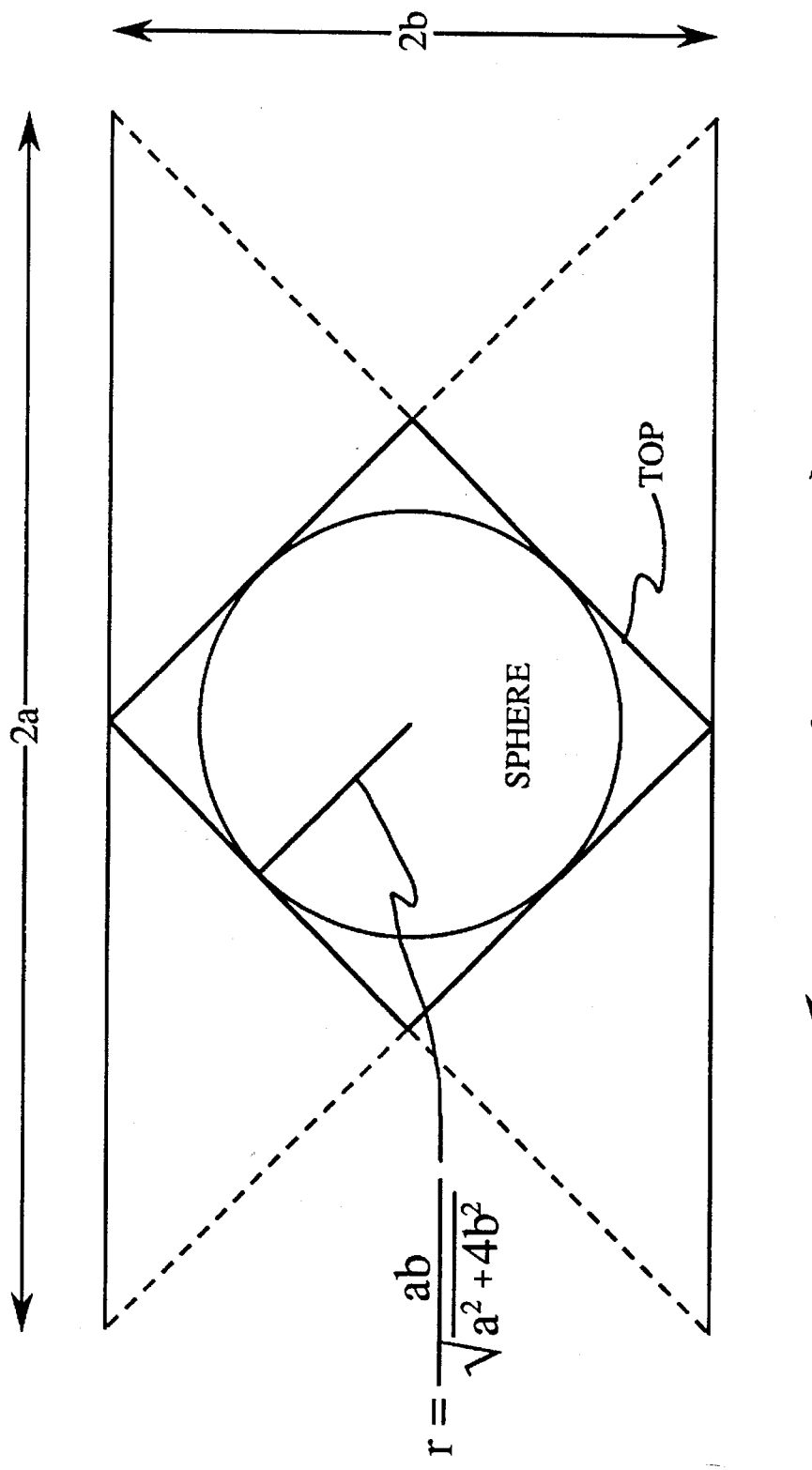
FIG. 9 illustrates the design of a tetrahedral scanning trajectory whose convex hull encloses objects of various shapes.
Figure 10:
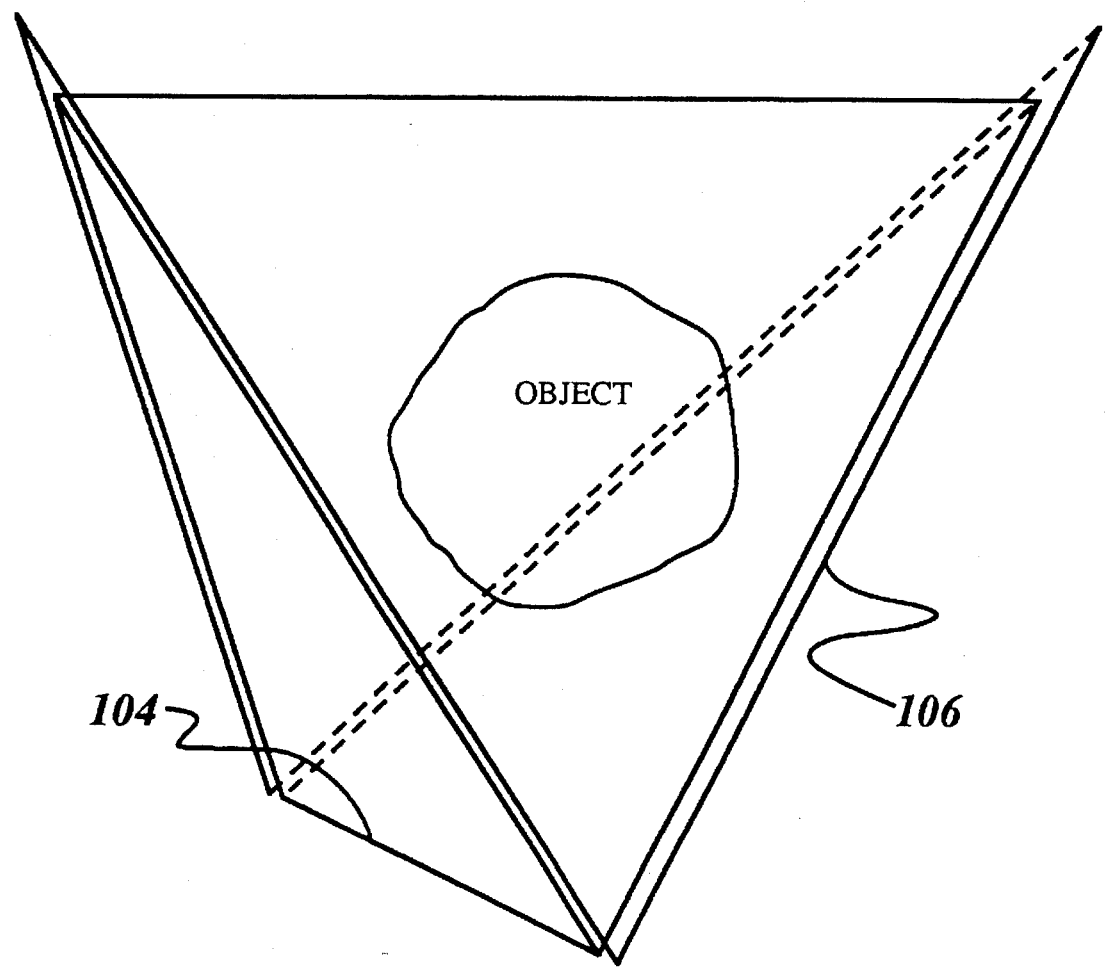
FIG. 10 exemplifies a complete, three dimensional, closed scanning trajectory comprising four straight line segments which are nowhere disconnected, arranged to accommodate continuous scanning along four non-intersecting edges of a tetrahedron enclosing an object.

Proper choice of three dimensional tetrahedral scanning trajectory begins by designing the smallest (i.e. closest fitting) tetrahedron that will enclose the object. The tetrahedron is defined by as few as three line segments. Such a tetrahedron is illustrated in FIG. 8. Note, the tetrahedron need not be regular, being defined only by an upper edge 102, a lower edge 104 and any connecting segment 106 which joins one end of the upper edge to one end of the lower edge. The convex hull so defined is a tetrahedron 108 enclosing object 110; thus, the three dimensional version of the completeness criterion is satisfied. Furthermore, any vertical two dimensional projection of the three dimensional scanning trajectory also encloses a projection of the object in the same plane. Consequently, the two dimensional version of the completeness criterion is also satisfied. It is possible to design such a tetrahedron to enclose any shape object; thus, it is possible to design a three segment complete scanning trajectory for any object. Consider the geometries illustrated in FIG. 9. Note for example:, a rotational symmetric object with a total height, 2b, and base diameter a; a sphere of radius $$ab/\sqrt{(a^2+4b^2)} \quad ;$$

cylinders of various dimensions ranging from a maximum height of 2b to a maximum diameter of a. These are but a few examples of object shapes that can be enclosed by a tetrahedron. It is further possible to close the three segment tetrahedral scanning trajectory by introducing another scan segment as shown in FIG. 10. Such a configuration may be more convenient in that the scan path is closed; although this is not necessary.

Applicant has restated a three dimensional completeness criterion in a more useful form and applied a two dimensional projection approach to aid visual analysis of a completeness assessment for candidate three dimensional scanning trajectories. An easy to implement, reliable method for determining whether or not a three dimensional scanning trajectory will provide complete Radon data for exact image reconstruction has been established. The method is practical and readily implemented to provide efficient scanning without unduly burdening commonly adopted scanning techniques.

While specific embodiments of the invention have been illustrated and described herein, it is realized that numerous modifications and changes will occur to those skilled in the art. It is therefore understood that the appended claims are intended to cover all modifications and changes as fall within the true spirit and scope of the invention.

What is claimed is:

1. A method for providing a three-dimensional scanning trajectory which satisfies a completeness criterion in three dimensions, for use in acquiring data which is to be used for exact image reconstruction of an object irradiated by a scanning cone beam source, said method comprising the steps of:

providing a candidate three-dimensional scanning trajectory which is nowhere disconnected having said source for traversing the scanning trajectory in a continuous manner from start point to end point;

projecting an external surface having edges defined by said candidate scanning trajectory, said external surface forming a convex hull;

assessing whether said convex hull encloses said object; and selecting said candidate scanning trajectory for use in acquiring data only if said convex hull is shown by said assessing step to enclose said object, to ensure that a complete set of data is acquired.

2. A method in accordance with claim 1 wherein said three dimensional scanning trajectory comprises exclusively a plurality of interconnected linear segments.

3. A method in accordance with claim 2 wherein said three dimensional scanning trajectory compromises a plurality of linear segments which collectively define the external surface of a tetrahedron enclosing said object.

4. A method for providing a three-dimensional scanning trajectory which satisfies a completeness criterion in three dimensions for use in acquiring data which is to be used for exact image reconstruction of an object irradiated by a scanning cone beam source, said method comprising the steps of:

providing a candidate three-dimensional scanning trajectory which is nowhere disconnected having said source for traversing the scanning trajectory in a continuous manner from start point to end point;

providing a planar projection of said candidate three-dimensional scanning trajectory;

providing a corresponding planar projection of said object;

assessing whether said projection of said object is enclosed by said projection of said candidate scanning trajectory; and selecting said candidate scanning trajectory for use in acquiring data only if said projection of said object is shown by said assessing step to be enclosed by said scanning trajectory projection.

5. A method in accordance with claim 4 wherein:

said assessing step comprises visually assessing said planar projections to determine whether said projection of said object is enclosed by said projection of said candidate scanning trajectory.

6. A method in accordance with claim 4 wherein said three dimensional scanning trajectory further compromises at least an upper edge, a lower edge and a connecting edge.

7. The method of claim 6 wherein:

said scanning trajectory comprises a plurality of linear segments which collectively define the external surface of a tetrahedron enclosing said object.

8. A method for constructing a three-dimensional scanning trajectory satisfying a completeness criterion in three dimensions for exact image reconstruction of an object irradiated by a scanning cone beam source, said method comprising the teps of:

providing a three-dimensional scanning trajectory which is traversed by said source in a continuous manner from start point to end point, said trajectory comprising exclusively a plurality of interconnected linear segments, and being nowhere disconnected;

projecting an external surface having edges defined by said scanning trajectory, said external surface enclosing said object; and scanning said object within said external surface such that any planar section through said object necessarily intersects said external surface.

* * * * *